(12) United States Patent
Björling

(10) Patent No.: US 7,953,487 B2
(45) Date of Patent: May 31, 2011

(54) HEART STIMULATING DEVICE

(75) Inventor: Anders Björling, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 76 days.

(21) Appl. No.: 11/917,799

(22) PCT Filed: Jun. 16, 2005

(86) PCT No.: PCT/SE2005/000944
§ 371 (c)(1),
(2), (4) Date: Aug. 10, 2009

(87) PCT Pub. No.: WO2006/135292
PCT Pub. Date: Dec. 21, 2006

(65) Prior Publication Data
US 2009/0306733 A1 Dec. 10, 2009

(51) Int. Cl.
*A61N 1/00* (2006.01)
(52) U.S. Cl. .......................................................... 607/18
(58) Field of Classification Search .................... 607/14, 607/18, 21, 22, 24
See application file for complete search history.

(56) References Cited

U.S. PATENT DOCUMENTS

| 4,410,132 A | | 10/1983 | Levine |
| 4,719,920 A | | 1/1988 | Alt et al. |
| 4,803,987 A | * | 2/1989 | Calfee et al. ..................... 607/24 |
| 4,926,863 A | | 5/1990 | Alt |
| 5,044,366 A | * | 9/1991 | Alt ................................. 607/18 |
| 5,336,244 A | | 8/1994 | Weijand |
| 5,564,434 A | | 10/1996 | Halperin et al. |
| 6,473,640 B1 | | 10/2002 | Erlebacher |
| 6,821,249 B2 | | 11/2004 | Casscells, III et al. |
| 7,389,142 B2 | * | 6/2008 | Holmstrom ..................... 607/18 |
| 2004/0147982 A1 | | 7/2004 | Bardy |

FOREIGN PATENT DOCUMENTS

WO WO 2004/026131 4/2004

* cited by examiner

*Primary Examiner* — George Manuel
*Assistant Examiner* — Robert N Wieland
(74) *Attorney, Agent, or Firm* — Schiff Hardin LLP

(57) ABSTRACT

An implantable heart stimulating device for indicating congestive heart failure (CHF) has a processor, an activity sensor that generates an activity signal indicative of a patient's activity, and a blood temperature sensor that measures blood temperature inside the heart of the patient and generates a temperature signal indicative of the measured temperature. From the activity signal and the temperature signal, the processor identifies a characteristic dip in the temperature signal related to a predetermined increase in the activity signal. The processor determines a CHF indicator value indicating the degree of CHF based on the magnitude of the temperature sensor dip for at least two increased activity levels.

8 Claims, 2 Drawing Sheets

HEART STIMULATING DEVICE

BACKGROUND OF THE INVENTION

1. Field of the Invention

The present invention relates to a heart stimulating device having the capability for measurement and qualification of the degree of congestive heart failure. The determined congestive heart failure indicator value—alone or together with other metrics—may advantageously be use in assessing the patient's status, titrating drugs and/or evaluating therapy.

2. Description of the Prior Art

Approximately 23 million people worldwide are afflicted with congestive heart failure (CHF), and 2 million new cases of CHF are diagnosed each year worldwide. In contrast to other cardiovascular disorders that have actually declined during the past few decades, the incidence of heart failure is one that rises. It is, in fact, the most rapidly growing cardiovascular disorder in the United States.

Congestive heart failure is a chronic inability of the heart to maintain an adequate output of blood from one or both ventricles of the heart to meet the metabolic demands of the tissues. With a markedly weakened left ventricle or right ventricle or both, the volume of blood presented to the heart is in excess of the heart's capacity to move it along. Consequently, fluid builds up behind the heart. With a weakened left ventricle or right ventricle or both, there is a shift of large volumes of blood from the systemic circulation into the pulmonary (lung) circulation. If the inability to move the volume of blood forward is due to a left heart side problem without the right side falling as well, blood continues to be pumped into the lungs by the normal right heart side, while it is not pumped adequately out of the lungs by the left heart side. As the volume of blood in the lungs increases, the pulmonary vessels enlarge, pulmonary venous congestion develops, and, once the pulmonary capillary pressure rises above a critical point, fluid begins to filter out of the capillaries into the interstitial spaces and alveoli (air sacs in the lungs where exchange of oxygen and carbon dioxide occurs), resulting in pulmonary oedema. Subsequently this can lead to pleural effusion (effusion is the escape of fluid into a part) and abdominal effusion. If the abnormality lies in the right heart side or the pulmonary arteries, limiting the ability to move blood forward, then congestion occurs behind the right heart side (causing pleural effusion and/or build up of fluid in the abdomen).

Although advances in pharmacology have led to better treatment, 50% of the patients with the most advanced stage of heart failure die within a year. Typically, heart failure patients receive several chronic oral therapies, including diuretics, ACE inhibitors, beta-blockers and inotropic agents.

A majority of patients are treated with drug therapy, but for patients with advanced CHF, device-based therapy or transplantation are their only alternatives. A large number of patients with advanced CHF have received left ventricular assist devices, and a number of promising technologies, including biventricular pacing and defibrillators, ventricular remodelling, and ventricular assist devices represent exciting, growing markets.

U.S. Pat. No. 6,821,249 relates to a temperature monitoring of congestive heart failure patients as an indicator of worsening condition by using the analysis of the speed and pattern of temperature change in a way that is individualized toward patient's health condition. Body sites to measure body temperature can be characterized as "core" or "peripheral" sites, meaning deep inside the body or near the surface, but even sites classified in that manner do not necessarily behave in the same way. Temperature sensors may be any temperature sensor known that is practically applicable, and include thermocouples, resistance temperature detectors or thermistors, thermosensitive chromophores, thermosensitive liquid crystals, infrared detectors and ultrasound detectors.

U.S. Pat. No. 6,821,249 also discusses the influence of the patient's activity that is suitably monitored by an accelerometer or a vibration sensor that provides a signal that upon conversion to digital form is usable by a microprocessor for an adjustment to a temperature attribute or to the sensitivity of detection of that attribute. The same concepts for adjusting a temperature reading or sensitivity of a cut-off point apply as for medications, including use of a learning algorithm to personalize the effect of temperature change from different levels of activity.

At the onset of physical activity, the amount of blood reaching heart from the outer extremities is increased. As the temperature of the blood in the outer extremities is lower, there is a dip in the temperature of the blood in the heart. After the dip, the temperature rises with time to a level above the initial as a cause of the activity. The maximal increase in temperature as a result of activity is approximately 1.5° C.

The temperature dip at the onset of activity is patient dependent, but especially pronounced in CHF patients. This is e.g. described in "Cardiac Pacing and ICDs", 3rd edition, Kenneth A. Ellenbogen & Mark A. Wood, page 110.

U.S. Pat. No. 4,719,920 discloses an exercise-responsive rate-adaptive cardiac pacemaker adapted to distinguish between physiologically determined changes of the patient's blood temperature under conditions of exercise and non-exercise. The pacemaker is also capable of recognizing the blood temperature dip which is characteristic of the commencement of exercise.

SUMMARY OF THE INVENTION

An object of the present invention is to provide a heart stimulating device having an improved capability of monitoring CHF and in particular temporal changes of the degree of CHF.

The above object is achieved in accordance with the present invention by an implantable heart stimulating device with the capability of indicating a degree of congestive heart failure, having a processor, an activity sensor that generates an activity signal indicative of patient activity, and a blood temperature sensor that measures blood temperature inside the heart and generates a temperature signal indicative of the measured temperature. The activity signal and the temperature signal are supplied to the processor, and the processor identifies a characteristic dip in the temperature signal that is related to the activity signal measured at the same time. Multiple temperature signal dips are determined respectively for different levels of activity, and the processor determines a congestive heart failure indicator value, indicative of the degree of congestive heart failure, based on a relationship between the identified temperature dip magnitudes respectively at the different activity levels.

Thus, the present invention is based upon the correlation of the activity level (e.g. measured by using an activity sensor of a heart stimulating device) and the initial decrease in temperature, "temperature dip", measured by a temperature sensor of a ventricular lead, and by using this correlation to determine (calculate) a CHF indicator value indicating the degree of CHF.

DESCRIPTION OF THE PREFERRED EMBODIMENTS

Figure 1:
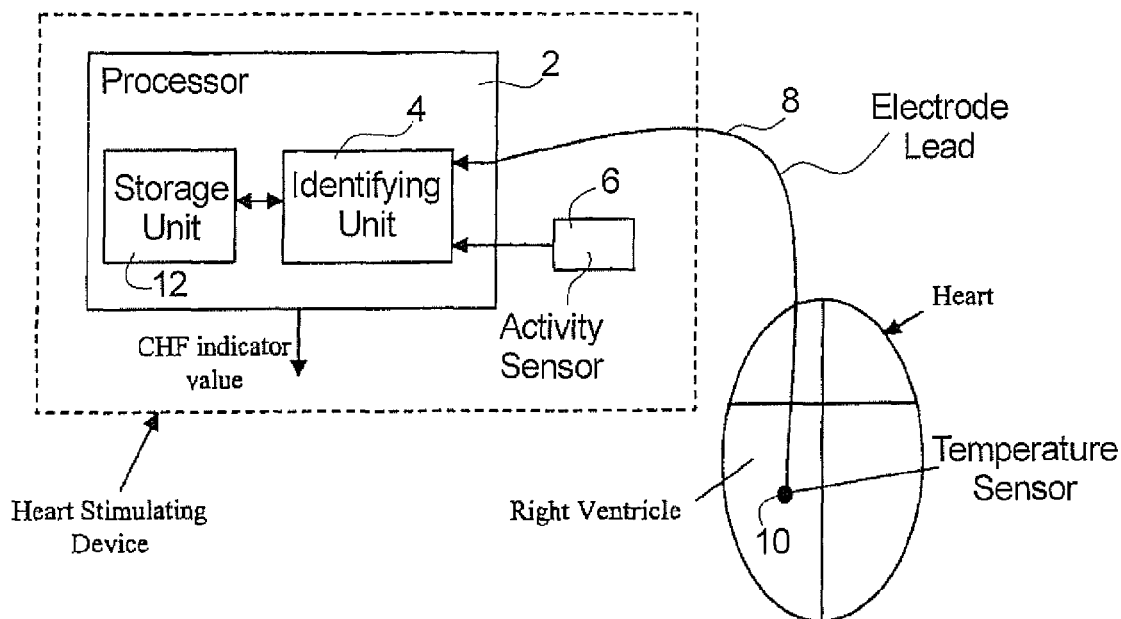
FIG. 1 schematic block diagram illustrating a preferred embodiment of the present invention.

FIG. 1 is a schematic block diagram illustrating a preferred embodiment of the present invention. In FIG. 1 is illustrated an implantable heart stimulating device for indicating congestive heart failure (CHF) having a processor 2, an activity sensor 6 for generating an activity signal in relation to patient activity, and a blood temperature sensor 10 adapted to measure blood temperature inside the heart and for generating a temperature signal in dependence of the measured temperature. The activity signal and temperature signal are applied to the processor 2 that is provided with an identifying unit 4 adapted to identify a characteristic dip in the temperature signal related to a predetermined increase of the activity signal and also to measure the magnitude of the dip. The processor 2 then determines a CHF indicator value indicating the degree of CHF based upon the magnitude of the temperature signal dip, wherein the indicator value is determined in relation to previously measured temperature signal dips for that patient. Preferably, the heart stimulating device has an electrode lead 8 adapted to apply stimulation pulses to the heart tissue and provided with the blood temperature sensing means.

Examples of suitable temperature sensors may be found in the above-cited U.S. Pat. No. 6,821,249 and in U.S. Pat. No. 5,336,244 and U.S. Pat. No. 5,564,434 that illustrate typical examples of a temperature sensor mounted on a ventricular lead which is applicable when realizing the present invention.

The activity sensor preferably is housed within the casing of the stimulating device. Preferably, the activity sensor uses a known form of miniature piezoelectric crystal in the form of a weighted cantilever arm to detect movement of the patient. A suitable form of such an element is disclosed, for example, in U.S. Pat. No. 4,140,132, but it will be understood that other known types of activity or motion sensors may alternatively be used. When the patient moves, the weighted cantilever arm undergoes vibration and the vibrations are converted to electrical signals by the piezoelectric crystal.

The patient's intrinsic P-wave rate, or the rate and/or volume of respiration as measured by impedance may also be used as a measure of activity.

Figure 2:
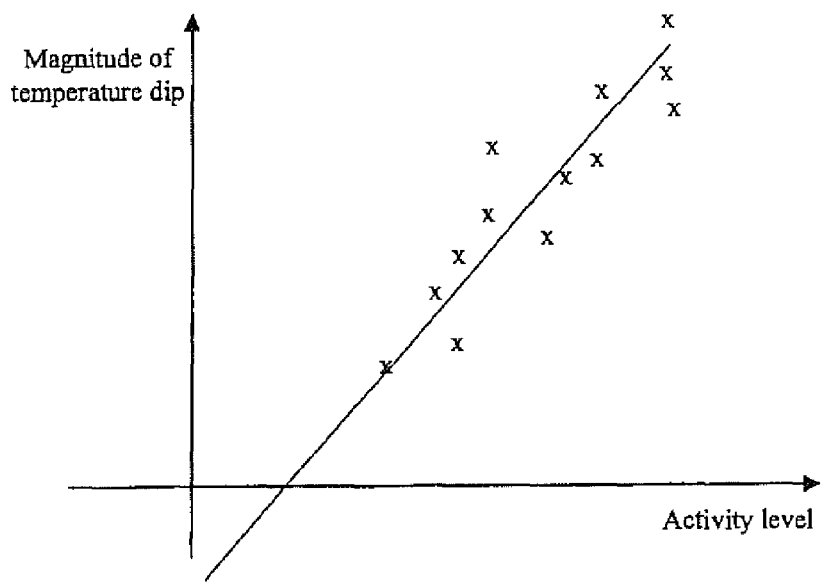
FIG. 2 shows a diagram illustrating the correlation between the magnitude of the dip in temperature and level of activity.

Preferably, a linear relationship between the activity and temperature signals is determined, and that linear relationship is used to determine the CHF indicator value. FIG. 2 shows a diagram illustrating the correlation (a linear relationship) between the magnitude of the dip in temperature and level of activity. A number of measure points (indicated with "x") of the magnitude of the temperature dip and corresponding activity level are marked in the diagram and a line having the slope k is determined by using a suitable mathematical method. For example the N last observations (N may be any number larger than 5) may be used to determine the slope of the curve which then is used as a CHF indicator value. The equation of the line is expressed as:

$$\text{magnitude of temperature dip} = k*(\text{activity level}) + m,$$

where m is a constant.

In a preferred embodiment the slope k is used to determine the CHF indicator value such that a higher magnitude of the temperature signal dip in correlation with an increased activity signal, i.e. a larger k (a steeper line) results in an increased CHF indicator value indicating a higher degree of CHF.

In addition, the CHF indicator value may directly be determined in dependence of the quotient between the magnitude of the temperature signal dip and the activity signal.

According to an alternative embodiment a non-linear model may be used in order to properly fit a curve to the measure points. In such a model e.g. a second order equation may be used.

The magnitude of the temperature signal dip is related to a normal temperature value being the base level of the temperature during normal conditions. Typical values of the magnitude of the dip are in the range of 0.12 to 0.25 degree C. for non-CHF patients. The base level may be determined in many different ways. In one embodiment the base level is determined as an average temperature value obtained during periods when the activity signal indicates that the activity level is below a threshold indicating low activity. According to another embodiment the base level is permanently set to a fixed value that need not be patient specific.

With references to FIG. 1 the processor includes a storage unit 12 where the activity signal and temperature signal are stored and that the determination of a congestive heart failure indicator value indicating the degree of CHF is performed at a later time.

The heart stimulating device illustrated in FIG. 1 naturally includes further components, e.g. a battery, communicating (telemetry) circuitry, etc., omitted in FIG. 1 for clarity.

According to a preferred embodiment the determination of the CHF indicator value is performed, e.g. at the time of follow-up, in an external programmer (not shown) outside the patient and in that case the activity and temperature values are transmitted from the implant to the programmer by known communication circuitry. Preferably, the programming means is provided with a display means (not shown).

Figure 3:
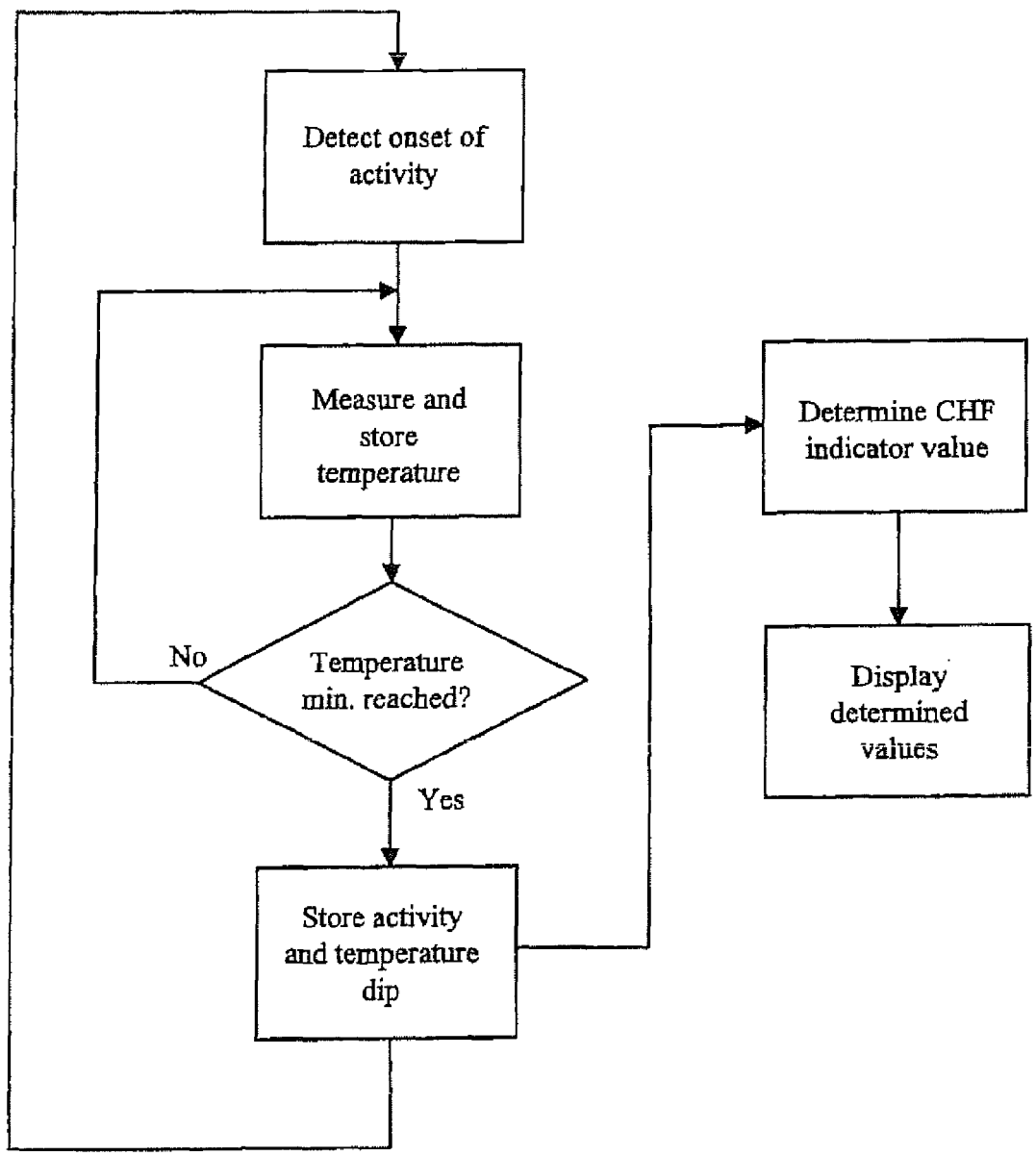
FIG. 3 shows a flow chart illustrating a preferred embodiment of the present invention.

FIG. 3 shows a flow chart illustrating a preferred embodiment of the present invention.

When the onset of activity is detected, the temperature of the ventricular blood is analyzed. The decrease in temperature compared to a normal value (the magnitude of the dip) is stored together with the corresponding activity level and these pairs of values are then stored and the CHF indicator value is determined.

As the temperature dip is patient dependent, each patient will act as their own control and the CHF indicator value may be used to track the regression or progression of the CHF, but may not be used to compare the CHF status of two patients.

Primarily the heart stimulating device according to the present invention relates to a pacemaker but may also be a cardioverter or defibrillator.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable heart stimulating device comprising:
   an activity sensor configured to interact in vivo with a living subject to detect physical activity of the subject and to generate and emit an activity signal indicative of said activity;
   a blood temperature sensor configured to interact in vivo with the subject to measure blood temperature inside the heart of the subject and to generate and emit a temperature signal indicative of the measured blood temperature; and a processor connected to said activity sensor and to said blood temperature sensor that receives said activity signal and said temperature signal therefrom, respectively, and said processor, from said activity signal, being configured to detect at least two onsets of activity by the subject and, for each of said at least two onsets of activity, to correlate a magnitude of a characteristic dip in the measured blood temperature represented in said temperature signal with a corresponding activity level, to thereby obtain at least two respective correlation points and, from said at least two correlation points, to generate an indicator value representing a degree of congestive heart failure of the subject, and to make said indicator value available as an output of the processor.

2. A heart stimulating device as claimed in claim 1 comprising a tissue stimulator including an electrode lead configured for implantation to deliver stimulation pulses to tissue associated with the heart, said blood temperature sensor being carried on said electrode lead.

3. A heart stimulating device as claimed in claim 1 wherein said processor is configured to identify a linear relationship between said at least two correlation points, and uses said linear relationship to determine said indicator value.

4. A heart stimulating device as claimed in claim 1 wherein said processor, upon identifying a larger magnitude of characteristic dip correlated with an increase in said activity, is configured to generate a higher indicator value indicating a higher degree of congestive heart failure.

5. A heart stimulating device as claimed in claim 1 wherein said processor is configured to reference said magnitude to a normal temperature value of said blood temperature inside the heart during an activity level designated as a baseline activity level.

6. A heart stimulating device as claimed in claim 1 comprising a storage unit in which said activity signal and said temperature signal are stored, and wherein said processor is configured to determine said indicator value from the stored activity signal and the stored temperature signal at a time separated from a time at which the activity signal and the temperature signal were obtained.

7. An implantable heart stimulating device comprising:
an activity sensor configured to interact in vivo with a living subject to detect physical activity of the subject and to generate and emit an activity signal indicative of said activity;
a blood temperature sensor configured to interact in vivo with the subject to measure blood temperature inside the heart of the subject and to generate and emit a temperature signal indicative of the measured blood temperature; and
a processor that receives said activity signal and said temperature signal from said activity sensor and said blood temperature sensor, respectively, and said processor being configured to detect an onset of activity by said subject from said activity signal and, thereafter, to identify a characteristic dip of the measured blood temperature following said onset of activity and to determine a magnitude of said characteristic dip, and to identify a value of said activity signal occurring contemporaneously with said characteristic dip, and to determine an indicator value representing a degree of congestive heart failure of the subject as a quotient of said magnitude of said characteristic dip and said contemporaneously occurring value of the activity signal, and to make said indicator value available at an output of the processor as an electronic output signal.

8. A heart stimulating device as claimed in claim 7 wherein said processor is configured to determine at least one further indicator value and to make a comparison between said indicator value and said at least one further indicator value to identify a progression of congestive heart failure of the subject, and to represent said progression of congestive heart failure of the subject as a further electronic output signal from the processor.

* * * * *